(12) United States Patent
Liu et al.

(10) Patent No.: US 12,136,485 B2
(45) Date of Patent: Nov. 5, 2024

(54) ELECTRONIC DEVICE AND METHOD FOR DETERMINING MEDICAL IMAGES

(71) Applicant: Industrial Technology Research Institute, Hsinchu (TW)

(72) Inventors: Hsiao-Wei Liu, Hsinchu County (TW); Tseng-Wei Lai, New Taipei (TW); Sen-Yih Chou, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 387 days.

(21) Appl. No.: 17/563,060

(22) Filed: Dec. 28, 2021

(65) Prior Publication Data

US 2023/0178219 A1   Jun. 8, 2023

(30) Foreign Application Priority Data

Dec. 2, 2021 (TW) ................. 110144968

(51) Int. Cl.
*G16H 30/40* (2018.01)
*G06N 20/20* (2019.01)
*G06V 10/774* (2022.01)
*G16H 50/20* (2018.01)

(52) U.S. Cl.
CPC ............. *G16H 30/40* (2018.01); *G06N 20/20* (2019.01); *G06V 10/774* (2022.01); *G16H 50/20* (2018.01)

(58) Field of Classification Search
CPC ........ G16H 30/40; G16H 50/20; G06N 20/20; G06N 3/045; G06N 3/08; G06V 10/774; G06V 10/25; G06V 10/764; G06V 10/82; G06V 2201/03
See application file for complete search history.

(56) References Cited

U.S. PATENT DOCUMENTS

| 10,949,975 | B2 | 3/2021 | Bogoni et al. |
| 2015/0159428 | A1* | 6/2015 | Johnson ............... E06B 7/14 49/471 |
| 2018/0260951 | A1 | 9/2018 | Yang et al. |
| 2018/0315188 | A1* | 11/2018 | Tegzes ............... G06T 7/11 |
| 2020/0202507 | A1* | 6/2020 | Ceccaldi ............... G06N 3/006 |
| 2020/0273166 | A1 | 8/2020 | Shaw |
| 2021/0125724 | A1* | 4/2021 | Kawahara ........... G16H 50/20 |

(Continued)

FOREIGN PATENT DOCUMENTS

| CN | 108986891 | 12/2018 |
| CN | 112349392 | 2/2021 |

(Continued)

OTHER PUBLICATIONS

"Office Action of Taiwan Counterpart Application", issued on Sep. 30, 2022, p. 1-p. 11.

*Primary Examiner* — Md K Talukder
(74) *Attorney, Agent, or Firm* — JCIPRNET (57) ABSTRACT

An electronic device and a method for determining medical images are provided. The method includes: obtaining an input image; inputting the input image into a first machine learning model to generate a labeled image, wherein the labeled image includes a plurality of area images; inputting the labeled image into a second machine learning model to generate a plurality of area determination data corresponding to the plurality of area images; and displaying a determination result including the plurality of area determination data.

12 Claims, 8 Drawing Sheets

(56) References Cited

U.S. PATENT DOCUMENTS

| | | | |
|---|---|---|---|
| 2023/0100179 A1* | 3/2023 | Haas | G06N 20/20 |
| | | | 382/159 |
| 2023/0153377 A1* | 5/2023 | Braun | G06V 10/82 |
| | | | 702/1 |
| 2023/0178219 A1* | 6/2023 | Liu | G06V 10/25 |
| | | | 382/128 |

FOREIGN PATENT DOCUMENTS

| | | |
|---|---|---|
| CN | 113516614 | 10/2021 |
| TW | 709147 | 11/2020 |
| TW | 202110387 | 3/2021 |

* cited by examiner

| | Training area image | Average | Standard deviation | Width | Length | Training area determination data |
|---|---|---|---|---|---|---|
| 1 | 601 | 37.63 | 26.9 | 57 | 46 | Grade2 |
| 2 | 602 | 37.11 | 26.0 | 63 | 37 | Grade1 |
| 3 | 603 | 36.31 | 22.08 | 61 | 27 | Grade2 |
| 4 | 604 | 40.59 | 26.41 | 59 | 28 | Grade1 |
| 5 | 605 | 40.2 | 27.25 | 54 | 27 | Grade1 |
| 6 | 606 | 40.27 | 24.51 | 54 | 21 | Grade2 |

ELECTRONIC DEVICE AND METHOD FOR DETERMINING MEDICAL IMAGES

CROSS-REFERENCE TO RELATED APPLICATION

This application claims the priority benefit of Taiwan application serial no. 110144968, filed on Dec. 2, 2021. The entirety of the above-mentioned patent application is hereby incorporated by reference herein and made a part of this specification.

TECHNICAL FIELD

The disclosure relates to an electronic device configured to determine medical images and a method for determining medical images.

BACKGROUND

Currently, when a doctor determines (diagnoses with) medical images, the doctor has to label the medical images manually. In addition, the determination (diagnosis) can only be performed by manually observing the characteristics in the medical images. However, it may not be easy to read the medical images due to photographing equipment or different photographing angles. How to efficiently determine (diagnose with) the medical images is a key technical issue in the field.

SUMMARY

The disclosure provides an electronic device and a method for determining medical images capable of increasing efficiency of determining the medical images.

The electronic device of the disclosure configured to determine the medical images includes a storage device, an input/output device, and a processor. The storage device stores a first machine learning model and a second machine learning model. The processor is coupled to the input/output device and the storage device. The processor is configured to obtain an input image and input the input image into the first machine learning model through the input/output device to generate a labeled image. The labeled image includes a plurality of area images. The processor is further configured to input the labeled image into the second machine learning model to generate a plurality of area determination data respectively corresponding to the plurality of area images. A determination result including the plurality of area determination data is displayed through the input/output device.

The method of the disclosure for determining medical images includes the following. An input image is obtained. The input image is input into a first machine learning model to generate a labeled image. The labeled image includes a plurality of area images. The labeled image is input into a second machine learning model to generate a plurality of area determination data respectively corresponding to the plurality of area images. A determination result including the plurality of area determination data is displayed.

Based on the above, in the electronic device and the method for determining medical images of the disclosure, multiple areas in the input medical images may be labeled by adopting a machine learning model, and the area determination data of the areas are generated by adopting the machine learning model. In addition, if there is an error between the multiple labeled areas, the reliability of further area determination data may be enhanced by adopting an area correction image. Therefore, the efficiency of determining the medical images is increased.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1:
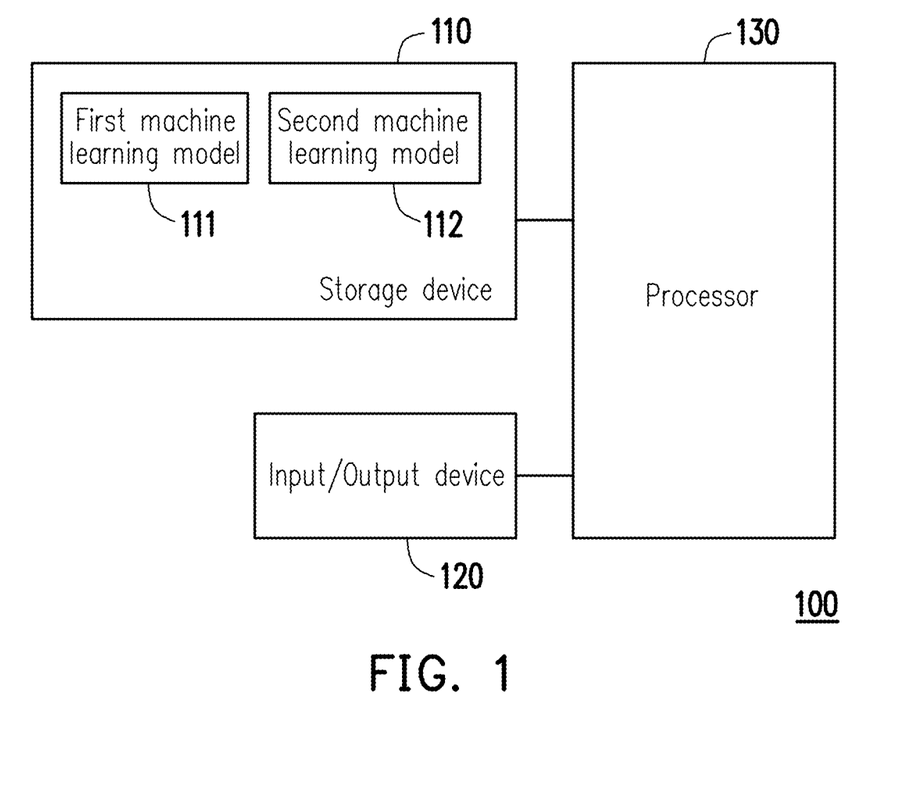
FIG. 1 is a block diagram of an electronic device configured to determine medical images according to an exemplary embodiment of the disclosure.

FIG. 1 is a block diagram of an electronic device 100 configured to determine medical images according to an exemplary embodiment of the disclosure.

Referring to FIG. 1, the electronic device 100 includes a storage device 110, an input/output device 120, and a processor 130.

The storage device 110 may be any type of fixed or mobile random access memory (RAM), read only memory (ROM), flash memory, hard disk drive (HDD), or other similar devices, or a combination thereof. In the exemplary embodiment, the storage device 110 stores a first machine learning model 111 and a second machine learning model 112. The first machine learning model 111 and/or the second machine learning model 112 are, for example, very deep convolutional networks for large-scale image recognition (VGG), a convolutional neural network (CNN), a recurrent neural network (RNN), or a long short term memory (LSTM) RNN.

The input/output device 120 is coupled to the processor 130 and is configured to transmit a signal. The processor 130 may receive an input signal or transmit an output signal through the input/output device 120. The input/output device 120 is, for example, a various input/output device such as a mouse, a keyboard, a screen, a touch panel, and/or a speaker.

The processor 130 is coupled to the storage device 110 and the input/output device 120 to control operation of the electronic device 100. In the exemplary embodiment, the processor 130 is, for example, a general purpose processor, a specific purpose processor, a conventional processor, a digital signal processor (DSP), multiple microprocessors, one or more microprocessors integrated with a DSP core, a controller, a micro-controller, an application specific integrated circuit (ASIC), a field programmable gate array (FPGA), any other type of integrated circuit, a state machine, an advanced RISC machine-based (ARM) processor or the like.

Figure 2:
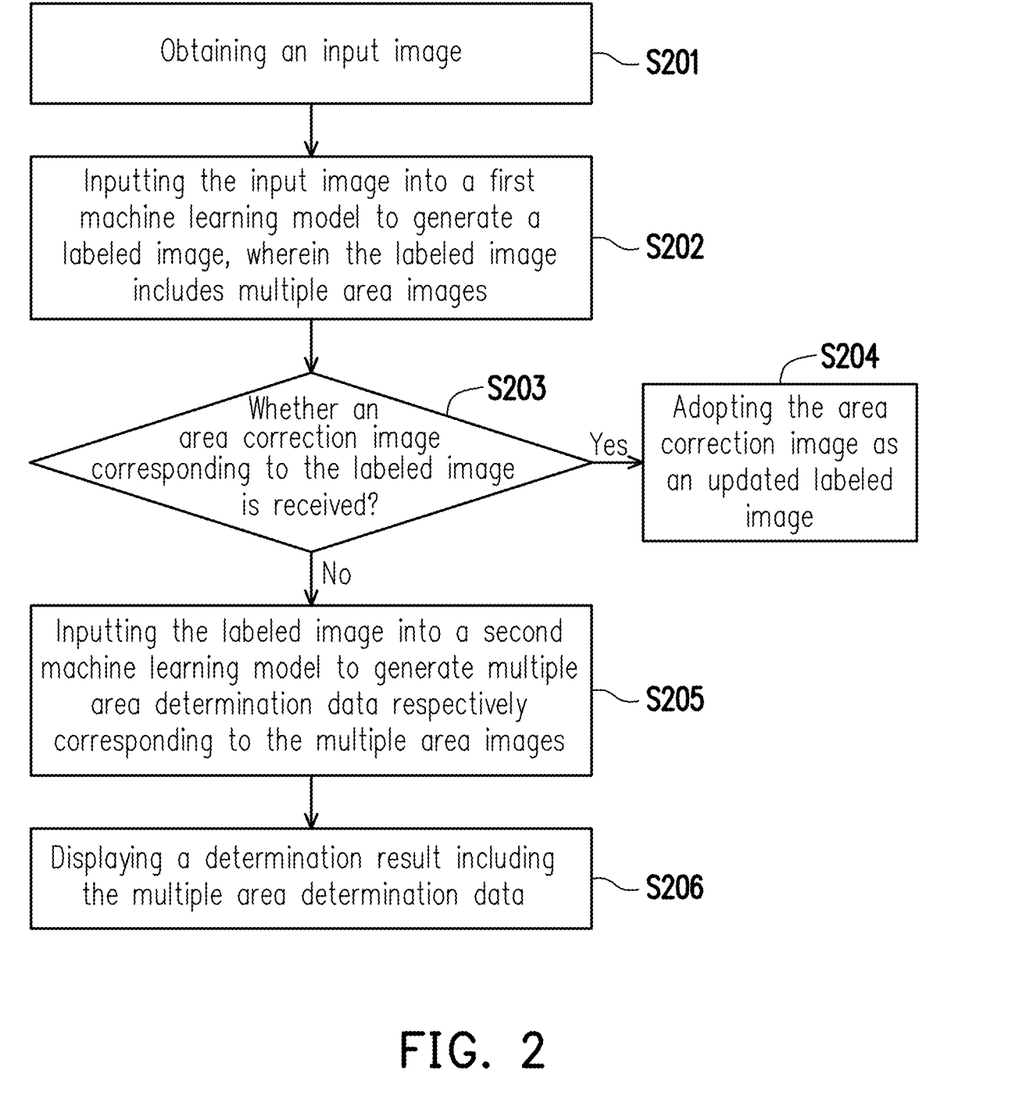
FIG. 2 is a flow chart of a method for determining medical images according to an exemplary embodiment of the disclosure.

FIG. 2 is a flow chart of a method for determining medical images according to an exemplary embodiment of the disclosure. In the exemplary embodiment, the method described in FIG. 2 is performed and implemented by the electronic device 100.

In step S201, the processor 130 obtains an input image through the input/output device 120. The input image of the exemplary embodiment may be an X-ray image, a CT image, or an MRI image. That is, the input image of the exemplary embodiment is a medical image to be determined (diagnosed).

In an exemplary embodiment, the processor 130 may train the first machine learning model 111 by adopting a first training dataset. The first training dataset may include a plurality of training labeled images respectively corresponding to a plurality of training images.

Figure 3:
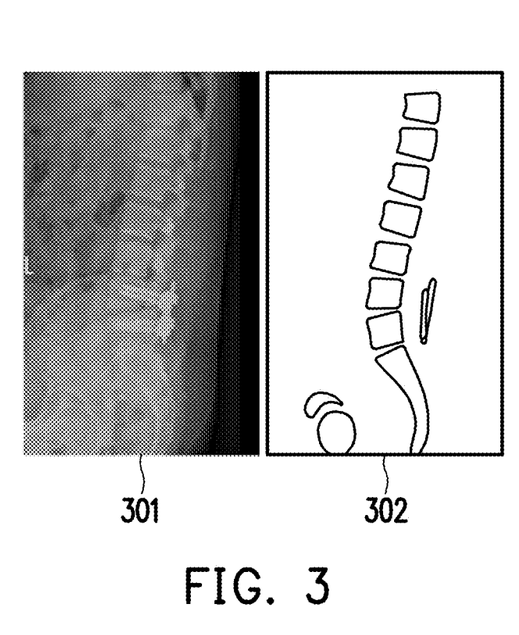
FIG. 3 is a schematic diagram of a first training dataset according to an exemplary embodiment of the disclosure.

FIG. 3 is a schematic diagram of a first training dataset according to an exemplary embodiment of the disclosure.

One of training data in the first training dataset may be a training labeled image 302 corresponding to a training image 301 (an X-ray image of a vertebral column) of FIG. 3. The training labeled image 302 may generated by manually labelling on the training image 301.

In step S202, the processor 130 may input the input image into the first machine learning model 111 to generate a labeled image. The labeled image includes a plurality of area images.

Figure 4A:
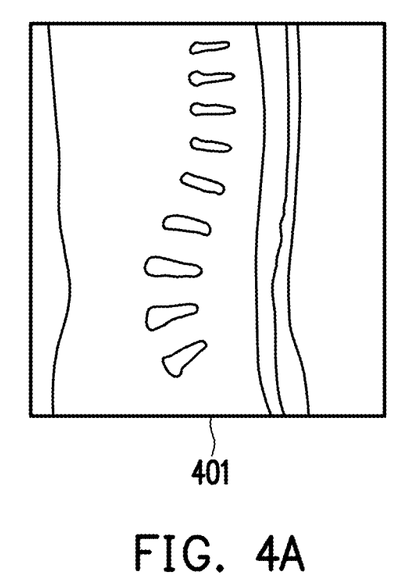
FIG. 4A and FIG. 4B are schematic diagrams of a labeled image according to an exemplary embodiment of the disclosure.
Figure 4B:
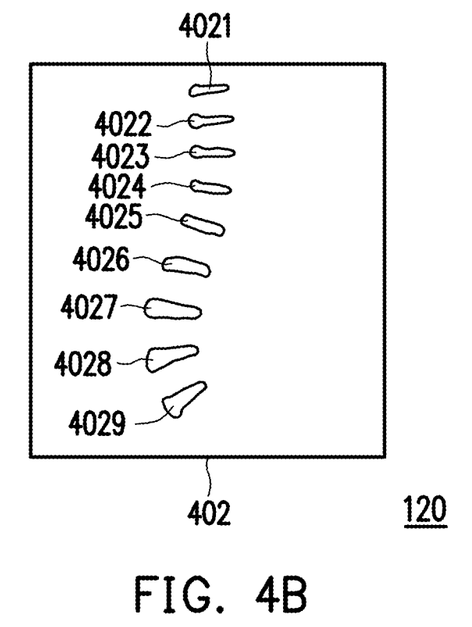

FIG. 4A and FIG. 4B are schematic diagrams of a labeled image according to an exemplary embodiment of the disclosure.

The processor 130 may input an input image 401 shown in FIG. 4A into the first machine learning model 111 to generate a labeled image 402 shown in FIG. 4B. The labeled image 402 may include an area image 4021, an area image 4022, . . . , and an area image 4029.

In an exemplary embodiment, the processor 130 may display the labeled image 402 through the input/output device 120 as shown in FIG. 4B for a doctor to examine. The doctor may examine the labeled image 402 and input an area correction image through the output device 120. For example, if the doctor finds the area image 4022 and the area image 4029 in the labeled image 402 incorrect, the doctor may draw the correct area image 4022 and the correct area image 4029 through the output device 120 and adopt the area image 4021, the correct area image 4022, the area image 4023, . . . , the area image 4028, and the correct area image 4029 as the area correction images through the output device 120.

In response to receiving the area correction image corresponding to the labeled image through the input/output device 120, the processor 130 may adopt the area correction image as an updated labeled image.

Specifically, in step S203, the processor 130 may determine whether the area correction image corresponding to the labeled image is received through the input/output device 120.

If the processor 130 determines that the area correction image corresponding to the labeled image is received through the input/output device 120 (a determination result in step S203 is "yes"), in step S204, the processor 130 may adopt the area correction image as the updated labeled image. Next, in step S205, the processor 130 may input the updated labeled image into the second machine learning model 112 to generate a plurality of area determination data respectively corresponding to the plurality of area images.

In an exemplary embodiment, the processor 130 may obtain a labeled error by using the labeled image 402 generated by the first machine learning model 111 and the area correction image (manually input by the doctor) and compare the labeled error and a predetermined threshold value of the labeled error.

In response to the labeled error being greater than the threshold value of the labeled error, the processor 130 may add the area correction image corresponding to the input image into the first training dataset to train the first machine learning model 111. In other words, since an error of the labeled image 402 generated by the first machine learning model 111 and the area correction image (manually input by the doctor) is too large, the processor 130 may add the input image and the area correction image into the first training dataset to train the first machine learning model 111.

If the processor 130 determines that the area correction image corresponding to the labeled image is not received through the input/output device 120 (the determination result in step S203 is "no"), in step S205, the processor 130 may input the labeled image into the second machine learning model 112 to generate the plurality of area determination data respectively corresponding to the plurality of area images.

In an exemplary embodiment, the processor 130 may train the second machine learning model 112 by adopting a second training dataset. The second training dataset may include a plurality of training area determination data respectively corresponding to a plurality of training area images.

Figure 5:
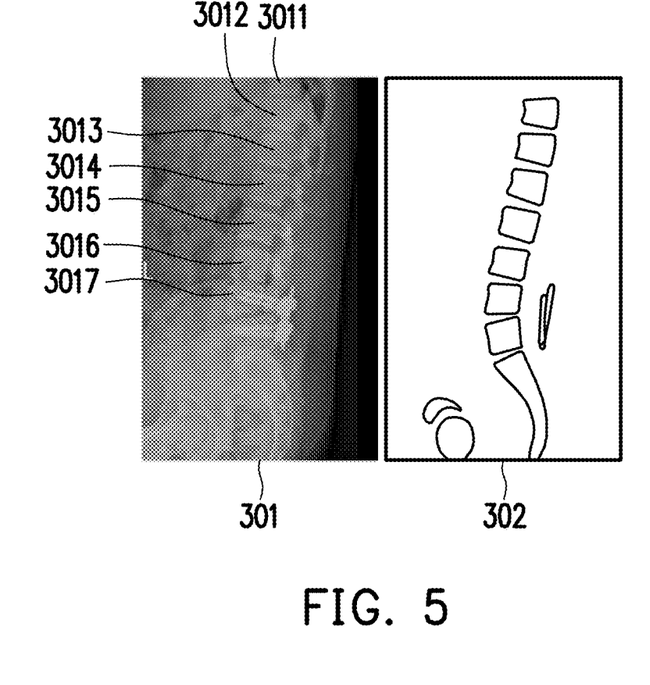
FIG. 5 is a schematic diagram of a training area image according to an exemplary embodiment of the disclosure.

FIG. 5 is a schematic diagram of a training area image according to an exemplary embodiment of the disclosure.

A training image 301 as shown in FIG. 5 may include a training area image 3011, a training area image 3012, . . . , and a training area image 3017. Specifically, the second training dataset configured to train the second machine learning model 112 may include the training area determination data respectively corresponding to the training area image 3011, the training area image 3012, . . . , and the training area image 3017. In the exemplary embodiment, after the processor 130 displays the training image 301 through the input/output device 120, the doctor may determine whether the training area image 3011, the training area image 3012, . . . , and the training area image 3017 are abnormal (and/or an abnormality grade) and adopt a determination result of each of the training area images as the training area determination data. For example, the training area determination data corresponding to the training area image 3011 may be at grade 2 (e.g. a grade/severity of lumbar degenerative disc disease is at grade 2).

In an exemplary embodiment, the processor 130 may calculate a plurality of training area dimensions respectively corresponding to the plurality of training area images. After the plurality of training area determination data respectively corresponding to the plurality of training area dimensions are added into the second training dataset, the processor 130 may use the second training dataset to train the second machine learning model 112.

Figure 6:
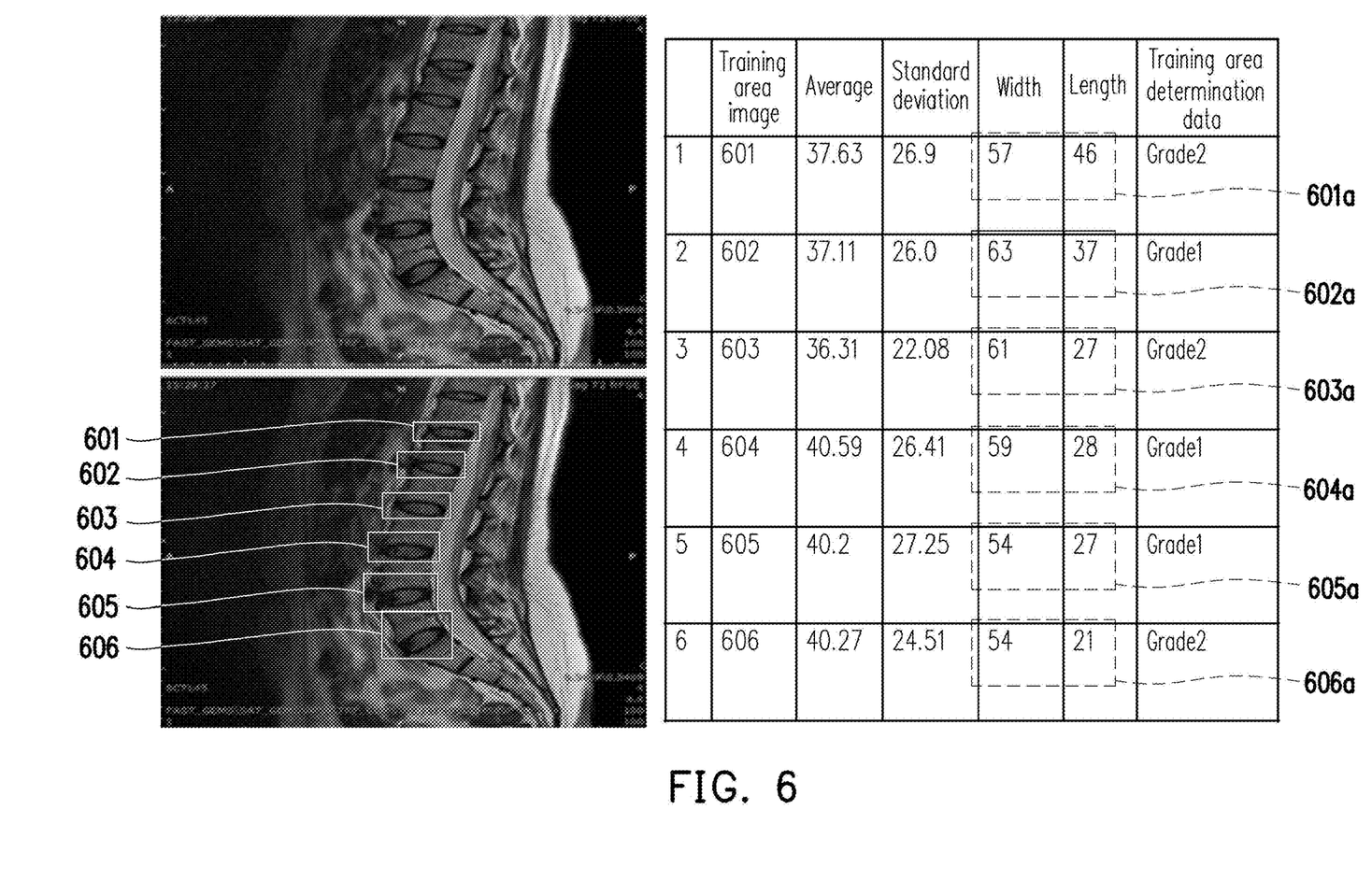
FIG. 6 is a schematic diagram of a training area image according to another exemplary embodiment of the disclosure.

FIG. 6 is a schematic diagram of a training area image according to another exemplary embodiment of the disclosure.

A labeled image shown in FIG. 6 may include a training area image 601, a training area image 602, . . . , and a training area image 606. The processor 130 may calculate the plurality of training area dimensions (e.g. a length and a width of each of the training area images) associated with the training area images. Next, the processor 130 may display a training area dimension 601*a* of the training area image 601, a training area dimension 602*a* of the training area image 602, . . . , a training area dimension 606*a* of the training area image 606 through the input/output device 120. In the exemplary embodiment, after the processor 130 displays the training area dimension 601*a* to the training area dimension 606*a* through the input/output device 120, the doctor may determine whether the training area image 601, the training area image 602, . . . , and the training area image 606 are abnormal (and/or the abnormality grade) and adopt the determination result of each of the training area images as the training area determination data through the input/output device 120. Based on the above, each of the training area determination data respectively corresponding to the training area images may be added into the second training dataset so that the processor 130 may use the second training dataset to train the second machine learning model 112.

Referring to FIG. 2 again, after the plurality of area determination data respectively corresponding to the plurality of area images are generated, in step S206, the processor 130 may display the determination result including the plurality of area determination data through the input/output device 120.

In an exemplary embodiment, the processor 130 may calculate a plurality of area dimensions associated with the plurality of area images. Next, the processor 130 may input the labeled image and the plurality of area dimensions into the second machine learning model 112 to generate the plurality of area determination data respectively corresponding to the plurality of area images. In other words, as described in the embodiments above, since the training data in the second training dataset (configured to train the second machine learning model 112) may be the training area determination data corresponding to the training area dimensions, the processor 130 may generate the area determination data by using the area dimensions and the second machine learning model 112.

Figure 7:
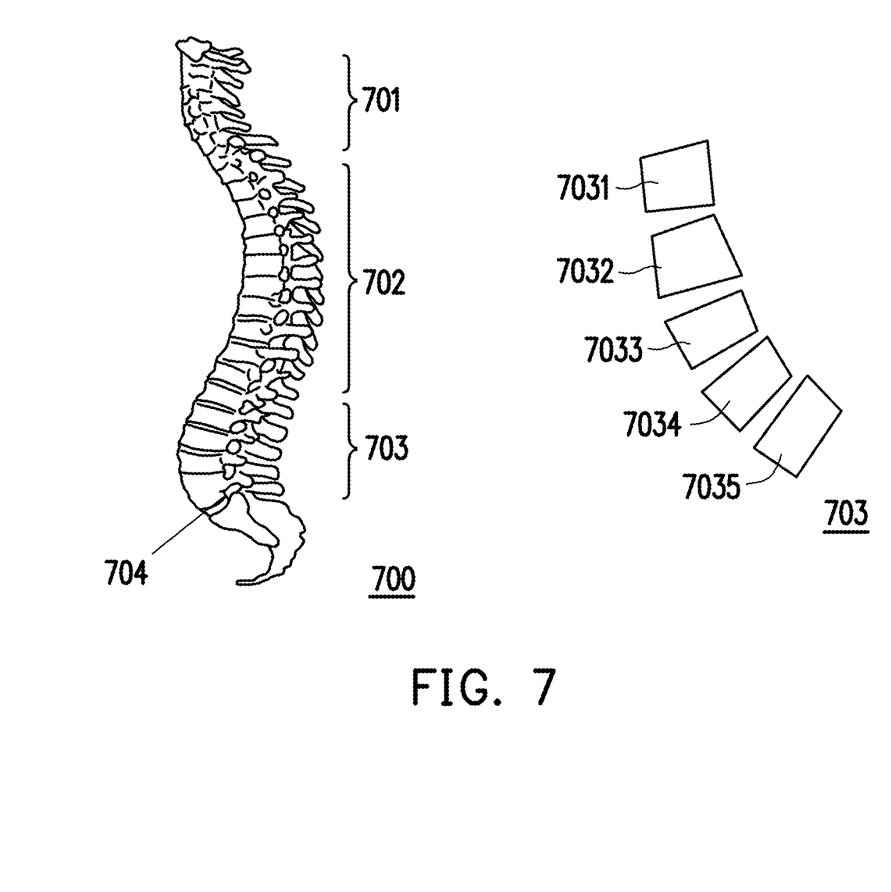
FIG. 7 is a schematic diagram of a human vertebral column according to an exemplary embodiment of the disclosure.

FIG. 7 is a schematic diagram of a human vertebral column according to an exemplary embodiment of the disclosure.

A human vertebral column 700 as shown in FIG. 7 may include a cervical vertebrae part 701, a thoracic vertebrae part 702, a lumbar vertebrae part 703, and a sacrum part 704. The lumbar vertebrae part 703 may include a vertebra 7031, a vertebra 7032, . . . , and a vertebra 7035.

In an exemplary embodiment, the processor 130 may calculate the plurality of area dimensions associated with the plurality of area images according to FIG. 7 and Table 1. Relevant details are further described below.

TABLE 1

| Area dimension item | Description |
| --- | --- |
| Area dimension L1 | An included angle between an upper edge and a lower edge of the vertebra 7031 |

TABLE 1-continued

| Area dimension item | Description |
| --- | --- |
| Area dimension L2 | An included angle between an upper edge and a lower edge of the vertebra 7032 |
| Area dimension L3 | An included angle between an upper edge and a lower edge of the vertebra 7033 |
| Area dimension L4 | An included angle between an upper edge and a lower edge of the vertebra 7034 |
| Area dimension L5 | An included angle between an upper edge and a lower edge of the vertebra 7035 |
| Area dimension L1-L2 | An included angle between a lower edge of the upper vertebra 7031 and an upper edge of the lower vertebra 7032 |
| Area dimension L2-L3 | An included angle between a lower edge of the upper vertebra 7032 and an upper edge of the lower vertebra 7033 |
| Area dimension L3-L4 | An included angle between a lower edge of the upper vertebra 7033 and an upper edge of the lower vertebra 7034 |
| Area dimension L4-L5 | An included angle between a lower edge of the upper vertebra 7034 and an upper edge of the lower vertebra 7035 |

Figure 8:
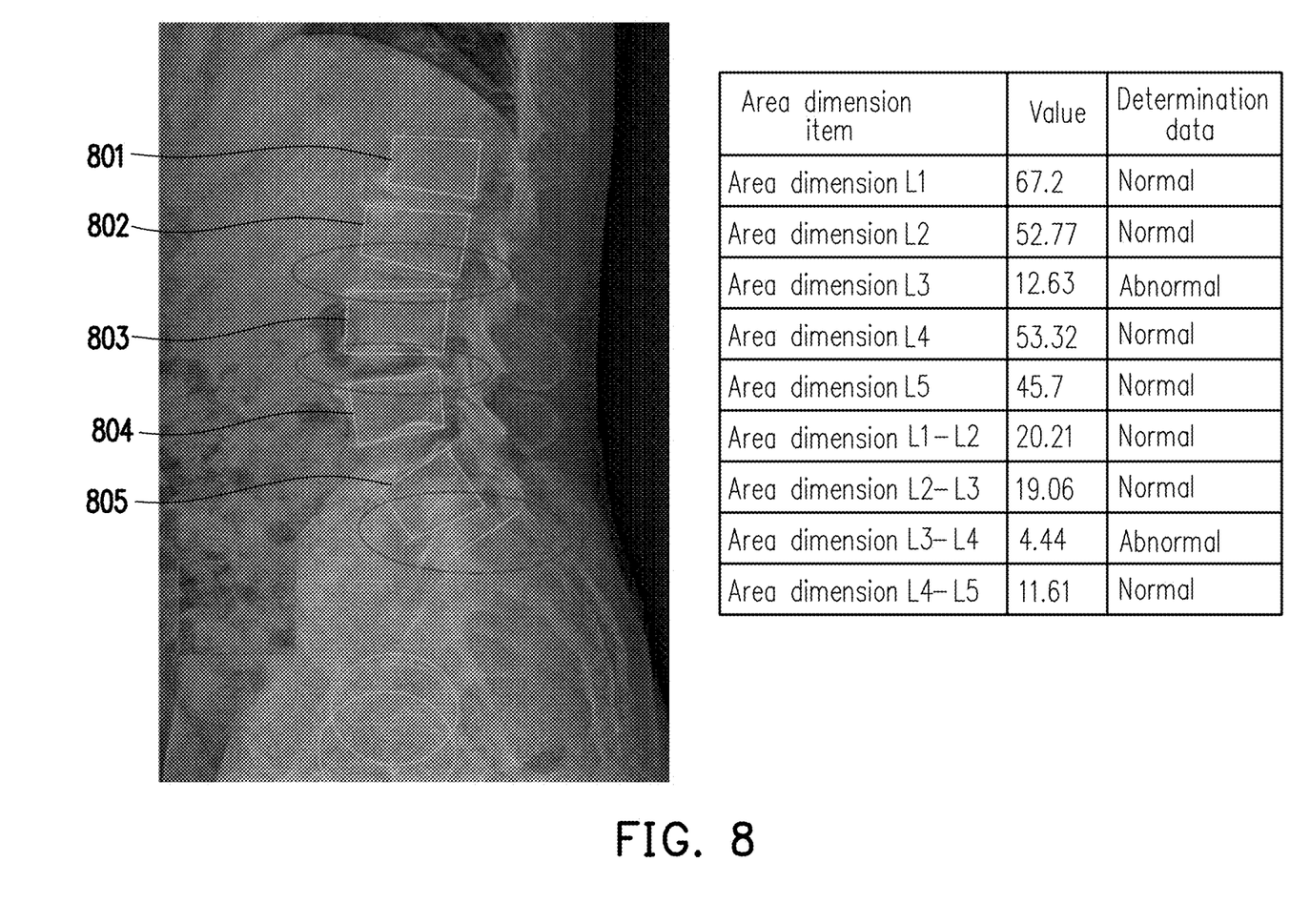
FIG. 8 is a schematic diagram of a determination result according to another exemplary embodiment of the disclosure.

FIG. 8 is a schematic diagram of a determination result according to another embodiment of the disclosure. In the exemplary embodiment, after the labeled image (of human lumbar vertebrae) as shown in FIG. 8 is generated by the first machine learning model 111, the processor 130 may calculate the plurality of area dimensions associated with area image 801, area image 802, . . . , and area image 805 according to FIG. 7 and Table 1. For example, the processor 130 may calculate an area dimension L1 by using the area image 801 (a position corresponding to the vertebra 7031), an area dimension L2 by using the area image 802 (a position corresponding to the vertebra 7032), and an area dimension L1-L2 by using the area image 801 and the area image 802.

The processor 130 may display each of the calculated area dimensions through the input/output device 120. Next, the processor 130 may input the labeled image including the area image 801, the area image 802, . . . , and the area image 805 as shown in FIG. 8 and each of the area dimensions into the second machine learning model 112 to generate the plurality of area determination data respectively corresponding to the plurality of area images and display the determination result including the plurality of area determination data and the plurality of area dimensions through the input/output device 120.

Note that the area dimension items shown in Table 1 are illustrative. The area dimension items may further include but not limited to pelvic incidence (PI), sacral slope (SS), pelvic tilt (PT), and the like.

In an exemplary embodiment, in step S201, the processor 130 may simultaneously obtain a plurality of input images and, through the method described in the embodiments above, simultaneously display the determination results of the input images through the input/output device 120 after the plurality of area determination data with respect to the input images are respectively generated. For example, the processor 130 may calculate a displacement value 1 of the vertebra 7031 and the vertebra 7032 in an input image 1 and calculate a displacement value 2 of the vertebra 7031 and the vertebra 7032 in an input image 2. If a difference between the displacement value 1 and the displacement value 2 is greater than the threshold value, the area determination data of the vertebra 7031 and the area determination data of the vertebra 7032 are determined to be abnormal.

In summary of the above, in the electronic device and the method for determining medical images of the disclosure, multiple areas in the input medical images may be labeled by adopting the machine learning model, and the area determination data are generated by adopting the machine learning model. In addition, if there is an error between the multiple labeled areas, the reliability of further area determination data may be enhanced by adopting the area correction image. Therefore, the efficiency of determining the medical images is increased.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. An electronic device configured to determine medical images, the electronic device comprising:
   a storage device storing a first machine learning model and a second machine learning model;
   an input/output device; and
   a processor coupled to the input/output device and the storage device,
   wherein the processor is configured to obtain an input image and input the input image into the first machine learning model through the input/output device to generate a labeled image, wherein the labeled image comprises a plurality of area images,
   wherein the processor is further configured to calculate a plurality of area dimensions associated with the plurality of area images and input the labeled image and the plurality of area dimensions into the second machine learning model to generate a plurality of area determination data respectively corresponding to the plurality of area images, wherein each of the plurality of area determination data is determined to be abnormal and to have abnormality grades if a difference between at least two of the area images is greater than a threshold value, and a determination result comprising the plurality of area determination data is displayed through the input/output device.

2. The electronic device configured to determine the medical images according to claim 1, wherein, in response to receiving an area correction image corresponding to the labeled image through the input/output device, the processor is further configured to adopt the area correction image as an updated labeled image, and the processor is further configured to input the updated labeled image into the second machine learning model to generate the plurality of area determination data respectively corresponding to the plurality of area images.

3. The electronic device configured to determine the medical images according to claim 2, wherein the processor is further configured to obtain a labeled error by using the labeled image and the area correction image, wherein, in response to the labeled error being greater than a threshold value of the labeled error, the processor is further configured to add the area correction image corresponding to the input image into a first training dataset.

4. The electronic device configured to determine the medical images according to claim 1, wherein the first machine learning model is trained by adopting a first training dataset comprising a plurality of training labeled images respectively corresponding to a plurality of training images.

5. The electronic device configured to determine the medical images according to claim 1, wherein the second machine learning model is trained by adopting a second training dataset comprising a plurality of training area determination data respectively corresponding to a plurality of training area images.

6. The electronic device configured to determine the medical images according to claim 1, wherein the processor is further configured to calculate a plurality of training area dimensions respectively corresponding to a plurality of training area images, wherein the second machine learning model is trained by adopting a second training dataset comprising a plurality of training area determination data respectively corresponding to the plurality of training area dimensions.

7. A method for determining medical images, the method comprising:
   obtaining an input image;
   inputting the input image into a first machine learning model to generate a labeled image, wherein the labeled image comprises a plurality of area images;
   calculating a plurality of area dimensions associated with the plurality of area images and inputting the labeled image and the plurality of area dimensions into a second machine learning model to generate a plurality of area determination data respectively corresponding to the plurality of area images, wherein each of the plurality of area determination data is determined to be abnormal and to have abnormality grades if a difference between at least two of the area images is greater than a threshold value; and
   displaying a determination result comprising the plurality of area determination data.

8. The method for determining the medical images according to claim 7, wherein inputting the labeled image into the second machine learning model to generate the plurality of area determination data respectively corresponding to the plurality of area images comprises:
   in response to receiving an area correction image corresponding to the labeled image through an input/output device, adopting the area correction image as an updated labeled image;
   inputting the updated labeled image into the second machine learning model to generate the plurality of area determination data respectively corresponding to the plurality of area images.

9. The method for determining the medical images according to claim 8, the method further comprising:
   obtaining a labeled error by using the labeled image and the area correction image;
   in response to the labeled error being greater than a threshold value of the labeled error, adding the area correction image corresponding to the input image into a first training dataset.

10. The method for determining the medical images according to claim 7, wherein the first machine learning model is trained by adopting a first training dataset comprising a plurality of training labeled images respectively corresponding to a plurality of training images.

11. The method for determining the medical images according to claim 7, wherein the second machine learning model is trained by adopting a second training dataset comprising a plurality of training area determination data respectively corresponding to a plurality of training area images.

12. The method for determining the medical images according to claim 7, the method further comprising:
   calculating a plurality of training area dimensions respectively corresponding to a plurality of training area images, wherein the second machine learning model is trained by adopting a second training dataset comprising a plurality of training area determination data respectively corresponding to the plurality of training area dimensions.

\* \* \* \* \*